United States Patent [19]
Ferket

[11] Patent Number: 5,516,798
[45] Date of Patent: May 14, 1996

[54] METHOD FOR TREATING DIARRHEA AND A COMPOSITION THEREFOR

[75] Inventor: Peter R. Ferket, Raleigh, N.C.

[73] Assignee: North Carolina State University, Raleigh, N.C.

[21] Appl. No.: 321,252

[22] Filed: Oct. 11, 1994

[51] Int. Cl.⁶ .................... A61K 31/685; A61K 31/205; A61K 31/195; A61K 31/045
[52] U.S. Cl. .................. 514/556; 514/76; 514/77; 514/564; 514/727; 514/867
[58] Field of Search .................. 514/76, 77, 556, 514/564, 727, 867

[56] References Cited

U.S. PATENT DOCUMENTS 5,182,299  1/1993  Gullans et al. .................. 514/460

OTHER PUBLICATIONS

Moeckel and Lien, "Bicarbonate Dependency of Betaine Synthesis in Cultured LLC–PK Cells", *Journal of the American Physiology Society*, vol. 266, No. 3, Part 2, pp. F512–515 (Mar., 1994).
Lien et al., "Characterization of Organic Osmolytes in Avian Renal Medulla: A Nonurea Osmotic Gradient System", *Journal of the American Physiology Society*, vol. 264, No. 6, Part 2, pp. R1045–1049 (Jun., 1993).
Prevenzyne®, "Physician's Desk Reference", pp. 1122–1123, (1987), Legere Pharmaceuticals, Scottsdale, Arizona.
Zypan®, "Physician's Desk Reference", p. 1972 (1987), Standard Process Laboratories, Inc., Milwaukee, Wisconsin.
Ilan et al., "Gastrointestinal Involvement in Homocystinuria", *Journal of Gastroenterology and Hepatology*, vol. 8, No. 1, pp. 60–62 (Jan.–Feb. 1993).
McGinnis et al., "Effect of Ethanolamine and Betaine on Perosis in Chicks", *Proc. Soc. Exp. Biol. Med.*, vol. 51, pp. 293–294 (1942).
Almquist and Grau, "Interrelation of Methionine, Choline, Betaine, and Arsenocholine in the Chick", *Journal of Nutrition*, vol. 27, pp. 263–269 (1944).
Saunderson et al., "Changes in Body–Weight, Composition and Hepatic Enzyme Activities in Response to Dietary Methionine, Betaine and Choline Levels in Growing Chicks", *British Journal of Nutrition*, vol. 63, pp. 339–349 (1990).
Ferket, "Flushing May Be Related to Growth Rate in Turkeys", *Turkey World*, pp. 10–11 (Apr.– May 1994).

Almquist and Grau, "Growth–Promoting Activity of Betaine in the Chick", *J. Bio. Chem.*, vol. 149, pp. 575–576 (1943).
Study Report, "Effect of Betaine on the Potentiation of an Ionophore Coccidiostate (Bio–Cox) in the Control of Coccidiosis for Growing Broiler Chickens" Aug. 25–Oct. 9, 1992.
Study report, "Effect of Betaine on the Potentiation of Bio–Cox in the Control of Coccidiosis for Growing Broiler Chickens and Comparison with Effect of Methionine", Aug. 25–Oct. 9, 1992.
Final Report Project No. PA–93–B1, "Effects of Betaine on Reduction of Coccidiosis when Fed With Bio–Cox to Male Broiler Chickens", Feb. 15–Mar. 7, 1993.
Summary Report, "Effects of Betaine on Broiler Performance and Carcass Quality When Given a Mild Infection of Coccidiosis" Apr. 29–Jun. 16, 1993.
Final Report Project No. PA–93–2, "Effects of Betaine on Broiler Performance and Carcass Quality When Given a Mild Infection of Coccidiosis", Apr. 29–Jun. 16, 1993.
Final Report Project No. PA–93–3, "Effects of Betaine on Ascites and Sudden Death Syndrome in Broilers", Apr. 8–May 26, 1993.
Final Report Project No. PA–93–4, "Comparison of the Effects of Betaine on Broiler Performance and Carcass Quality when Birds are Grown with or without an Experimentally Induced Coccidiosis Infection" Aug. 19–Oct. 8, 1993.
Trial 93–FIN–04–B Battery Study by James L. McNaughton, "Efficacy of Betaine in Improving Nutrient Utilization in Broiler Chicks 1–21 Days of Age During Coccidiosis" Aug. 17–Sep. 7, 1993.
Study, "Betaine For Weaning and Scoring" 1993.
Article from the "Poultry Health Handbook—2nd Edition" defining Perosis by L. Dwight Schwartz, D. V. M., p. 167, 1977.
Article entitled "Effects of Food Containing Betaine/Amino Acid Additive on the Osmotic Adaption of Young Atlantic Salmon, *Salmo salar L.*", by Virtanen et al. published in *Aquaculture*, vol. 83, pp. 109–122 (1989).

*Primary Examiner*—Kimberly Jordan
*Attorney, Agent, or Firm*—Richard E. Jenkins

[57] ABSTRACT

Described is a method of treating diarrhea in a warm-blooded vertebrate animal, and a composition therefor. The method involves administering to the animal an effective amount of a methylamine, such as betaine. Also described is the use of a composition for the manufacture of a medicament for treatment of diarrhea in a warm-blooded vertebrate animal, wherein the composition contains an effective amount of a methylamine, such as betaine.

17 Claims, No Drawings

METHOD FOR TREATING DIARRHEA AND A COMPOSITION THEREFOR

TECHNICAL FIELD

The present invention relates to a method and composition for treating diarrhea in animals. Also, the present invention relates to use of a composition for manufacture of a medicament for treating diarrhea in animals. More particularly, the invention relates to treating diarrhea in warm-blooded vertebrates, i.e. birds and/or mammals (including humans), wherein the diarrhea has resulted from pathogens, nutritional factors, environmental factors, and/or physiological disorders, with a methylamine.

Methylamines useful in the present invention include, but are not limited to, betaine, creatine, creatine phosphate, choline, phosphorylcholine, and glycerophosphorylcholine. Especially, betaine is useful in the present invention.

BACKGROUND OF THE INVENTION

More particularly, the formula of betaine is $(CH_3)_3N^+CH_2COO^-$. Betaine is known to be naturally present in many plants, especially sugar beets. Also, betaine is known to be naturally present in the kidneys of mammals, and, in particular, is one of the major renal organic osmolytes. See, for instance, Moeckel and Lien, *American Journal of Physiology*, Vol. 266, No. 3, Part 2 (March, 1994). Additionally, betaine is known to be naturally present as an organic osmolyte in the renal cortex and medullary cones of adult female domestic fowl. See, for instance, Lien, Pacelli, and Braun, "Characterization of Organic Osmolytes in Avian Renal Medulla: A Nonurea Osmotic Gradient System", *American Journal of Physiology*, Vol. 264, No. 6, Part 2 (June, 1993).

Moreover, a tablet containing betaine HCl, and also containing multiple digestive enzymes such as diastase, is sold under the trade name PREVENZYNE® from Legere Pharmaceuticals of Scottsdale, Ariz., and under the trade name ZYPAN® from Standard Process Laboratories, Inc. of Milwaukee, Wis., for the treatment in humans of flatulence, bloating, and fullness after eating food.

Of interest vis-a-vis methylamines such as betaine is U.S. Pat. No. 5,182,299, issued Jan. 26, 1993, to *Gullans and Heilig*, assignors to Brigham and Women's Hospital of Boston, Mass. More particularly, this patent involves a method of treating an osmotic disturbance in an animal by administering to the animal an organic osmolyte. The osmotic disturbances described are hyponatremia, chronic hyponatremia, central pontine myelinolysis associated with hyponatremia, osmotic disturbances associated with renal dialysis, diabetic ketoacidosis, hyperglycemic hyperosmolar coma, acute hypernatremia, chronic uremia, chronic hypernatremia, including accidental salt loading in high sodium dialysis or baby formula, diabetes insipidus, diabetes mellitus, alcoholism-related dehydration, dehydration from other causes, and AIDS. Diarrhea is not mentioned in the patent.

The '299 patent suggests that three classes of osmolyte compounds are useful in the method of treating an osmotic disturbance in an animal. The three classes are polyols, methylamines, and amino acids. However, only Laboratory Example VI in the '299 patent shows treatment of animals, but it is not treatment of live animals, as there are no laboratory examples of treatment of actual, live animals. Rather, slices of rabbit brain tissue were treated, and moreover, the treatment was only with myoinositol (a type of polyol) and/or with glutamine (a type of amino acid). There is no laboratory example showing either treatment of a live animal or of a tissue sample from a dead animal with a methylamine. The remainder of the laboratory examples do not show any kind of treatment, but rather show the natural presence of various osmolytes in certain tissues from rats and rabbits. Hence, there is no actual reduction to practice of the suggested treatment of live animals for osmotic disturbances. The patent only claims polyols in the method of treating an osmotic disturbance in an animal.

Of further interest in connection with betaine is a case study report by Ilan, Eid, Rivkind, Weiss, Dubin, and Yatziv, entitled "Gastrointestinal Involvement in Homocystinuria", published in the *Journal of Gastroenterology and Hepatology*, Vol. 8, No. 1, pp. 60–62 (January–February, 1993). In this case study, a young man of 17 years age having a genetic defect known as a cystathionine beta-synthase deficiency, which causes homocystinuria, developed the symptoms of chronic diarrhea and acute pancreatitis. The young man was treated with betaine which alleviated the diarrhea. Betaine, as noted in this article, is known as a methyl donor for the treatment of homocystinuria in beta-synthase deficient patients. In other words, the treatment of the patient with betaine was the treatment of his beta-synthase deficiency, which resulted in the deficiency no longer causing the symptom of diarrhea.

Moreover, betaine has been investigated for the treatment of perosis (hemorrhages and swelling of the hock that leads to a twisted metatarsal joint and slippage of the achilles tendon from the condyle) in chickens. See, McGinnis, Norris, and Heuser, "Effect of Ethanolamine and Betaine on Perosis in Chicks", *Proc. Soc. Exp. Biol. Med.*, Vol. 51, pp. 293–294 (1942). Also, betaine has been investigated for its effect on the growth of chickens. See, Almquist and Grau, "Growth-Promoting Activity of Betaine in the Chick", *J. Bio. Chem.*, Vol. 149, pp. 575–576 (1943); Almquist and Grau, "Interrelationship of Methionine, Choline, Betaine, and Arsenocholine in the Chick", *J. Nutr.*, Vol. 27, pp. 263–269 (1944); and Saunderson and Mackinlay, "Changes in body-Weight, Composition and Hepatic Enzyme Activities in Response to Dietary methionine, Betaine and Choline Levels in Growing chicks", *Br. J. Nutr.*, Vol 63, pp. 339–349 (1990). It is additionally interesting to note that betaine has been shown to reduce coccidiosis lesion score in the guts of broiler chickens.

OBJECTS AND SUMMARY OF THE INVENTION

The present invention provides a method of treating diarrhea in a warm-blooded vertebrate animal comprising administering to the animal an effective amount of a methylamine, such as a methylamine including, but not limited to, betaine, creatine, creatine phosphate, choline, phosphorylcholine, glycerophosphorylcholine, and combinations thereof.

Also, the present invention provides a composition for treating diarrhea in a warm-blooded vertebrate animal comprising an effective amount of a methylamine, such as a methylamine including, but not limited to, betaine, creatine, creatine phosphate, choline, phosphorylcholine, glycerophosphorylcholine, and combinations thereof, and at least one ingestible excipient or diluent carrier, the concentration of the methylamine being such that a daily dose provides between about 0.05 g to about 2.0 g of methylamine per kilogram of body weight of the animal.

Additionally, the invention provides for use of a composition for the manufacture of a medicament for treatment of diarrhea in a warm-blooded vertebrate animal, the composition comprising an effective amount of a methylamine, such as a methylamine including, but not limited to, betaine, creatine, creatine phosphate, choline, phosphorylcholine, glycerophosphorylcholine, and combinations thereof.

Thus, it is an object of the invention to stop diarrhea in animals, particularly in young animals that are infants or children, whereby the young animals can achieve the proper weight gain during growth into adulthood.

More particularly, it is a further object of the invention to stop diarrhea in birds, especially fowl such as turkeys, chickens, ducks, geese, guinea fowl, and the like, when they are young so that their maturity into adulthood is more efficacious. As a result, their maturity into adulthood occurs with fewer health-related problems and better feed conversion such that they can be more quickly sent to market for slaughter to produce high quality meat products.

Additionally, in connection with sending the animals to market for slaughter, the transportation causes stress which can cause diarrhea. Thus, it is a further object to treat animals with a methylamine, for instance betaine, just prior to slaughter in order to stop diarrhea induced by such stress and consequently to reduce carcass/meat contamination by fluid and fecal matter, particularly for fowl.

Hence, an advantage of the invention is that when the diarrhea is stopped, less contamination of equipment, the animal's pen, or the animal itself, by fecal matter occurs, whether at the farm, during transport to a slaughterhouse, or during processing at the slaughterhouse.

Some of the objects and advantages of the invention having been stated above, other objects and advantages will become evident as the description proceeds, when taken in connection with the accompanying Laboratory Examples as best described below.

DETAILED DESCRIPTION OF THE INVENTION

The present invention involves a method for treating diarrhea in an animal that is a warm-blooded vertebrate. Additionally, the invention also involves use of a composition for the manufacture of a medicament for the treatment of diarrhea in warm-blooded vertebrate animals. Therefore, the invention concerns mammals and birds.

Contemplated is the treatment of mammals such as humans, as well as those mammals of economical importance (animals raised on farms for consumption by humans) and/or social importance (animals kept as pets or in zoos) to humans, for instance, carnivores other than humans (such as cats and dogs), swine, ruminants (such as cattle, oxen, sheep, giraffes, deer, goats, bison, and camels), and horses.

Also, contemplated is the treatment of birds, which can include those kinds of birds kept in zoos. However, particularly contemplated is the treatment of fowl, and more particularly domesticated fowl, i.e., poultry, such as turkeys, chickens, ducks, geese, guinea fowl, and the like, as they are also of economical importance to humans.

Therefore, especially important is the treatment of diarrhea in livestock, including, but not limited to, swine, ruminants, horses, poultry, and the like.

More particularly, a treatment effective amount of a methylamine is administered to the warm-blooded vertebrate animal. Thus, the invention comprises administration of a methylamine in concentrations calculated to provide the animal being treated with the appropriate milieu to provide control or cessation of diarrhea.

All forms and metabolites of methylamines should be useful in the present invention. More specifically, methylamines useful in the present invention include, but are not limited to, betaine, creatine, creatine phosphate, choline, phosphorylcholine, and glycerophosphorylcholine, with betaine being preferred.

The chemical form of betaine may include, but is not limited to, betaine anhydride, betaine monohydrate, betaine hydrochloride, betaine sodium aspartate, and combinations thereof, with the anhydrous form of betaine being preferred.

The methylamine may be administered to the animal as a supplement to fluids that are administered enterally or parenterally, for instance nutriment fluids such as intervenous sucrose solutions. Furthermore, buccal or sublingual administration to the animal is also contemplated. Additionally, the methylamine may be administered to the animal by various oral methods, for instance as a tablet, capsule, or powder (crystalline form) that is swallowed. Also, oral administration may include that the methylamine is admixed in a carrier fluid appropriate therefor so that it is administered as a liquid (solution or suspension) that is drunk. When the methylamine is admixed in a carrier fluid, appropriate fluids therefor include, but are not limited to, water, rehydration solutions (i.e, water with electrolytes such as potassium citrate and sodium chloride, for instance the solution available under the trade name RESOL® from Wyeth Laboratories), nutritional fluids (i.e, milk, fruit juice), and combinations thereof. Thus, the oral administration of the methylamine may be as a component of the diet, such as human food, animal feed, and combinations thereof.

Hence, it is also contemplated that additional ingredients, such as various excipients, carriers, surfactants, nutriments, and the like, as well as various medicaments other than a methylamine, or combinations thereof, may be present together with the methylamine. Medicaments other than a methylamine may include, but are not limited to, osmolytic polyols and osmolytic amino acids (i.e., myo-inositol, sorbitol, glycine, alanine, glutamine, glutamate, aspartate, proline, and taurine), cardiotonics (i.e., glycocyamine), analgesics, antibiotics, electrolytes (i.e., organic or mineral electrolytes such as salts), and combinations thereof.

A suitable amount of methylamine for administration to the animal should range from about 0.05 gram to about 2.0 gram per kilogram of body weight of the animal per day, more preferably from about 0.10 gram to about 1.3 gram per kilogram of body weight of the animal per day, and even more preferably from about 0.25 gram to about 1.0 gram per kilogram of body weight of the animal per day. Of course, the amount can vary depending on the severity of the diarrhea and/or the age of the animal.

The present invention should be useful in the treatment of diarrhea in animals, wherein the diarrhea is caused by pathogens (i.e., parasites, bacteria, protozoa, and viruses, including toxic agents in food created by spoiling of the food,), nutritional factors (i.e., excess mineral salts, excess protein, allergic agents in food, undigestible food components, or poor quality ingredients in food), environmental factors that act as stressors or pollutants (i.e., heat, chilling, shipment of animals, or toxins such as from air and/or water pollution), and/or physiological disorders such as those of the digestive tract, pulmonary/circulatory system, liver, kidneys, and/or pancreas.

As described in the Laboratory Examples below, methylamines, particularly betaine, have been found to be especially useful in the treatment of diarrhea, known as flushing, in turkeys. As reported in an article entitled "Flushing May Be Related to Growth Rate in Turkeys", published in *Turkey World*, at pages 10 and 11 in April-May of 1994, and authored by Peter Ferket (the inventor of the present invention), turkeys as they grow from infancy to adulthood tend to exhibit flushing from an age of about 9 weeks to an age of about 16 weeks. Flushing is particularly observed in turkeys during the hot summer months, as the estimated temperature of comfort for young turkeys in this age range is from about 65° F. (about 18° C.) to about 50° F. (about 10° C.), with the lower temperature being the temperature of comfort at about the mid-point of the flushing time of about 12 weeks of age. Although not mentioned in "Flushing May Be Related to Growth Rate in Turkeys" to *Ferket*, it is interesting to note that it is known turkeys will shed a "spike" in oocysts from 11 to 17 weeks (77 to 117 days) of age, which corresponds with the observed flushing. Thus, as set out in the Laboratory Examples below, treatment of turkeys with betaine to control or stop diarrhea in the turkeys was investigated.

LABORATORY EXAMPLES

The anhydrous betaine employed in Examples I–IV below was betaine anhydrous feed grade, purchased under the trade name, BETAFIN BCR, from Finnsugar Bioproducts, Incorporated, of Schaumburg, Ill.

EXAMPLE I (treatment of male turkeys)

Forty-eight different flocks of male turkeys, ranging in age from 3 to 134 days, on various turkeys farms were treated for diarrhea using the anhydrous form of betaine. Specifically, a total of 699,525 male turkeys were treated by giving them an aqueous solution having betaine arthydride dispersed in it.

A dosage of 10 pounds of betaine/500 gallons of water (4.5 kg/1894 liters) was used continuously in the drinking water for 48 hours. Turkeys that were deemed cured for diarrhea were observed to have had normal fecal droppings within 24 hours after the betaine treatment was started.

More specifically, based on the weight of betaine in the water, and the amount of betaine that the turkeys were given to drink during the 48-hour period, the weight amount of betaine in g per kg body weight of turkey was calculated, using the number and average weight of the turkeys in the particular flock that was treated. All turkeys in any one particular flock were the same age in days, and therefore were approximately the same body weight.

In particular, betaine requests from the various turkey farms were used to determine the amount of betaine delivered to each farm that reported a diarrhea problem. It was assumed that the betaine treatment at 10 pounds/500 gallons was started within 1 day of the request date and that all the betaine was used during the treatment. Based on the inventory number of turkeys in each flock and the estimated body weight for age (using British United Turkeys of America standards for body weight), the amount of betaine used per unit body weight (g betaine/kg body weight) was calculated.

The effectiveness of the betaine treatment was dependent upon the age of the turkeys. All turkeys of 34 days or less in age were not cured from the diarrhea. Most of the turkeys ranging from 42 days to 70 days in age were cured, except that the flocks of turkeys that were 43 days, 69 days, and 70 days, were not cured by the treatment. All turkeys that were 71 days or more in age were cured.

Hence, of all turkeys treated, the betaine treatment cured 71% of the flocks treated for diarrhea. The diarrhea condition never reoccurred in most flocks, but in flocks in which diarrhea did reoccur later, betaine treatment was successful in stopping the condition.

Since the turkeys that were 34 days or younger in age were not cured, although it is not intended to be bound to any theory, it is believed that apparently either the cause of the diarrhea is different in younger as compared to older turkeys, or the dosage of betaine given the younger turkeys was not correct. Nevertheless, from the effect of the betaine dosage in the drinking water to treat diarrhea, an appropriate dosage to treat the diarrhea at different ages was estimated, as described in more detail below.

As noted above, all flocks of 71 days or more in age were cured. The average dosage used for this group was 0.5 g betaine/kg body weight with a standard deviation of 0.20 and a range of about 0.14 to 1.35 g/kg body weight. It is possible that a lower dosage may be effective in the younger turkeys because even the lowest dosage of 0.14 g betaine/kg body weight was effective in the age group of turkeys that were 71 days or older.

Apparently, the effect of dosage is likely an important factor, considering the results of betaine treatment dosage in turkeys of 70 days in age or younger. The following differences were noted in betaine treatment dosages used in the turkeys of 3–34 days age that did not respond, in the turkeys of 42–70 days age that did not respond, and in the turkeys of 42–70 days age that did respond to betaine treatment.

The very youngest turkeys (3–7 days in age) received a very high dosage (15.4 g/kg body weight) which may have resulted in some water palatability problems. Although it is not intended to be bound to any theory, since no turkeys in this age group were cured, it is postulated that the diarrhea problem observed in these young turkeys was either due to different causative agents than in the older turkeys, or the betaine dosage was too high, affecting water consumption rate. As to the second theory, possibly the high level of betaine in the water caused the water to have a taste aversive to the young turkeys, so that they simply did not drink much of the water and thus received only a de minimis amount of betaine that was too small to have an effect on the diarrhea, rather than their having received the calculated amount of betaine.

It is noted that the remainder of the young turkeys (11–34 days in age) still received a dosage of over 2 g betaine/kg body weight, which is far higher than any of the dosages given the older turkeys of 42 days age or more. Accordingly, it is possible the high amount of betaine resulted in the water tasting aversive to this group too, so that they refrained from drinking.

In older turkeys of 42–70 days of age, a treatment dosage of 0.6 g betaine/kg body was not effective, but a higher dosage of 1.0 g betaine/kg body weight was a treatment effective amount.

Based on these data, diarrhea-affected turkeys of 70 days of age or younger should be given a dosage of about 1 g betaine/kg body weight over a 24 hour period, whereas diarrhea-affected turkeys of 71 days of age or older should be given a dosage of about 0.5 g betaine/kg body weight over a 24 hour period.

Lastly, the following is noted in connection with the above-described treatment of turkeys. The seasonal effects of diarrhea in 10- to 16-week old turkeys may also be related to intestinal bloom of coccidiosis or other organisms. Supplementation of the turkey feed with an ioniphore coccidiostat (specifically, the antibiotic monensin, which is well known as a feed additive for poultry, was used in the turkey farm field operation that was the subject of the present experiment) had been stopped at 6 to 8 weeks (42 to 56 days) in age because sufficient immunity should have developed in the turkeys by then.

The results are summarized in Table I below, and it is noted that in the third and sixth columns of the table, betaine anhydride is abbreviated as BET.

TABLE I (male turkeys)

| FLOCK NUMBER | NUMBER OF BIRDS IN FLOCK | TOTAL BET (kg) SENT TO TURKEY FARM | AVERAGE BODY WEIGHT (kg) | AGE (DAYS) | CALCULATED BET PER BODY WEIGHT (g/kg) | FLOCK CURED (YES OR NO) |
|---|---|---|---|---|---|---|
| 786 | 11516 | 25 | 0.17 | 3 | 12.8 | NO |
| 790 | 24363 | 75 | 0.17 | 7 | 18.1 | NO |
| 771 | 13870 | 25 | 0.34 | 11 | 5.30 | NO |
| 791 | 16523 | 25 | 0.34 | 13 | 4.45 | NO |
| 783 | 19124 | 25 | 0.65 | 19 | 2.01 | NO |
| 765 | 25356 | 50 | 0.65 | 21 | 3.03 | NO |
| 748 | 12569 | 25 | 0.65 | 24 | 3.06 | NO |
| 775 | 11243 | 25 | 0.65 | 24 | 3.42 | NO |
| 753 | 11411 | 25 | 0.65 | 25 | 3.37 | NO |
| 730 | 20071 | 50 | 1.1 | 31 | 2.26 | NO |
| 754 | 10368 | 25 | 1.1 | 34 | 2.19 | NO |
| 720 | 13462 | 25 | 1.61 | 42 | 1.15 | YES |
| 715 | 10504 | 25 | 2.28 | 43 | 1.0 | NO |
| 725 | 36229 | 100 | 2.28 | 44 | 1.21 | YES |
| 701 | 10861 | 25 | 3.08 | 52 | 0.74 | YES |
| 721 | 18399 | 100 | 3.98 | 58 | 1.37 | YES |
| 719 | 27150 | 125 | 3.98 | 61 | 1.16 | YES |
| 717 | 13516 | 75 | 3.98 | 62 | 1.39 | YES |
| 703 | 18013 | 50 | 3.98 | 63 | 0.70 | YES |
| 687 | 12493 | 50 | 4.95 | 67 | 0.81 | YES |
| 708 | 12087 | 25 | 4.95 | 69 | 0.42 | NO |
| 684 | 10882 | 25 | 4.95 | 70 | 0.46 | NO |
| 41 | 7812 | 25 | 6 | 71 | 0.53 | YES |
| 670 | 12645 | 50 | 6 | 72 | 0.66 | YES |
| 699 | 9270 | 75 | 6 | 72 | 1.35 | YES |
| 40 | 9535 | 25 | 6 | 73 | 0.44 | YES |
| 38 | 14950 | 25 | 7.08 | 78 | 0.24 | YES |
| 662 | 14040 | 75 | 7.09 | 80 | 0.75 | YES |
| 672 | 12445 | 50 | 7.09 | 83 | 0.57 | YES |
| 653 | 19107 | 100 | 8.22 | 87 | 0.64 | YES |
| 654 | 10120 | 50 | 8.22 | 91 | 0.60 | YES |
| 631 | 13406 | 50 | 9.35 | 92 | 0.40 | YES |
| 658 | 10539 | 75 | 9.35 | 95 | 0.76 | YES |
| 644 | 10670 | 75 | 9.35 | 96 | 0.75 | YES |
| 640 | 18743 | 125 | 9.35 | 97 | 0.71 | YES |
| 622 | 11091 | 50 | 10.49 | 102 | 0.43 | YES |
| 615 | 18236 | 100 | 10.49 | 102 | 0.52 | YES |
| 609 | 9791 | 75 | 10.49 | 105 | 0.73 | YES |
| 591 | 11734 | 75 | 11.63 | 109 | 0.55 | YES |
| 619 | 15767 | 25 | 11.63 | 111 | 0.14 | YES |
| 621 | 12948 | 75 | 11.63 | 111 | 0.50 | YES |
| 647 | 14484 | 25 | 11.63 | 112 | 0.15 | YES |
| 618 | 11858 | 75 | 12.78 | 115 | 0.49 | YES |
| 588 | 11278 | 50 | 12.78 | 118 | 0.35 | YES |
| 584 | 15315 | 125 | 13.92 | 121 | 0.59 | YES |
| 594 | 23001 | 75 | 13.92 | 124 | 0.23 | YES |
| 597 | 10193 | 50 | 13.92 | 125 | 0.35 | YES |
| 595 | 10537 | 25 | 16.14 | 134 | 0.14 | YES |

Thus, the use of betaine in drinking water for the treatment of diarrhea was shown to be an effective method of controlling diarrhea in turkeys.

EXAMPLE II (treatment of female turkeys)

A flock of 6000 market hen turkeys on a turkey farm was treated for diarrhea using the anhydrous form of betaine in aqueous solution, in a manner similar to the above-described treatment of male turkeys. As all turkeys in the flock were the same age in days, they therefore were approximately the same body weight. Hence, they were administered betaine at a dosage of 10 pounds of betaine/500 gallons of water (4.5 kg/1894 liters) continuously in their drinking water for 24 hours. Based on the weight on betaine in the water and the amount thereof that the turkeys were given to drink over the 24 hours, the weight amount of betaine in g per kg body weight of turkey was calculated, using the average weight for age (using British United Turkeys of America standards for body weight) of the turkeys in the 6000-turkey flock.

The turkeys were treated twice, at an age of 69 days and of 93 days. Litter samples, comprising droppings and the pine shaving bedding, were collected from 6 places within the turkey house: southwest (SW), southeast (SE), center-south (CS), center-north (CN), northwest (NW), and northeast (NE). From each of the samples, the moisture content was determined by weighing the sample, drying it, and then re-weighing it. The moisture content was determined on each of 9 days over a period from when the turkeys were 69 days to 96 days in age.

The results are summarized in Table II below.

TABLE II

| | (female turkeys) | | | | | | | | |
|---|---|---|---|---|---|---|---|---|---|
| Age (days) | PERCENT OF MOISTURE CONTENT IN LITTER | | | | | | | | |
| Place | 69 | 72 | 75 | 78 | 82 | 85 | 89 | 92 | 96 |
| SW | 50 | 23.4 | 24.7 | 32.5 | 27.6 | 29.4 | 30.4 | 34.4 | 30.1 |
| SE | 50 | 33.1 | 29.6 | 31.9 | 28.2 | 32 | 31.2 | 33.8 | 32.2 |
| CS | 44.6 | 32.4 | 31.1 | 30.6 | 30.4 | 34.6 | 37.5 | 38.3 | 33 |
| CN | 37.8 | 35.4 | 24.7 | 26.3 | 32.2 | 32.9 | 36.4 | 40.1 | 31.9 |
| NW | 39.5 | 36.6 | 24.3 | 32 | 33.6 | 34.4 | 33.7 | 33.6 | 33.3 |
| NE | 53.3 | 39.2 | 28.6 | 28.7 | 31.6 | 35.1 | 31.9 | 30.4 | 32.1 |
| Avg | 45.9 | 33.4 | 27.2 | 30.3 | 30.6 | 33.1 | 33.5 | 35.1 | 32.1 |

As can be seen from the data in Table II, average litter moisture decreased significantly from over 45% to below about 35% during the 20 days following the initial treatment with betaine anhydride. When average litter moisture reached 35.1% at the age of 92 days, the second treatment was performed at the age of 93 days, and subsequently, average litter moisture decreased to 32.1%.

If turkeys are having normal droppings and not diarrhea, the average moisture content should range from about 30% to about 35%, more preferably 30%. When the moisture content rises above 35%, the effects of clumping, ammonia build up, and excess microbial activity start to occur, and become worse as the moisture content continues to rise. Particularly, when the average litter moisture content rises above 40%, these effects will have adverse consequences on the good health and growth performance of turkeys.

Thus, the use of betaine in drinking water for the treatment of diarrhea was shown to be an effective method of controlling diarrhea in female turkeys.

EXAMPLE III (treatment of turkeys shortly prior to shipment to slaughterhouse)

At a turkey farm, turkeys were treated using the anhydrous form of betaine in aqueous solution, in a manner similar to the above-described treatment of turkeys, but only during the 24 hours immediately preceding shipment of the turkeys to a slaughterhouse. It is well known that the stress of being shipped causes turkeys to have diarrhea.

Approximately 300 male turkeys were treated by administering to them a dosage of 10 pounds of betaine anhydride per 500 gallons of water (4.5 kg/1894 liters) continuously in their drinking water for 24 hours prior to shipment. A control group of approximately 300 male turkeys was given plain water. For both groups, the water was removed right at the turkeys being caught for shipment, and the feed was removed 8 hours prior to the turkeys being caught for shipment.

The inspectors counted and recorded turkeys from both groups for fecal contamination, and visually noted less contamination for the treated turkeys. The results are summarized in Table III below.

TABLE III

| | (turkeys) | | |
|---|---|---|---|
| | Number of turkeys | | % of turkeys |
| | inspected | showing fecal contamination | showing fecal contamination |
| Control | 243 | 16 | 6.5 |
| Betaine | 260 | 4 | 1.5 |

The reduction from 6.5% of the control flock that exhibited fecal contamination to only 1.5% of the treated flock that exhibited fecal contamination is a significant reduction in contamination during shipment to market.

EXAMPLE IV (treatment of broiler chickens shortly prior to shipment to slaughterhouse)

A similar experiment was repeated as in Example III, but this time with broiler chickens instead of turkeys. At a farm, chickens were treated using the anhydrous form of betaine in aqueous solution, in a manner similar to the above-described treatment of turkeys, but only during the 24 hours immediately preceding shipment of the chickens to a slaughterhouse. It is well known that the stress of being shipped causes chickens to have diarrhea.

At the farm, 300 broiler chickens were divided into 3 groups of 100 chickens each. The treatment group was administered a dosage of 10 pounds of betaine anhydride per 500 gallons of water (4.5 kg/1894 liters) continuously in their drinking water for 24 hours prior to shipment. Each of the 2 control groups of chickens was given plain water. For all 3 groups, the water was removed right at the chickens being caught for shipment.

The inspectors counted and recorded chickens from all 3 groups for fecal contamination, and visually noted less contamination for the treated chickens. The results are summarized in Table IV below.

TABLE IV

| | (broiler chickens) | | |
|---|---|---|---|
| | Number of chickens | | % of chickens |
| | inspected | showing fecal contamination | showing fecal contamination |
| Control | 100 | 11 | 11 |
| Control | 100 | 18 | 18 |
| Betaine | 100 | 5 | 5 |

The reduction from 11% and 18%, respectively, of the 2 control flocks that exhibited fecal contamination to only 5% of the treated flock that exhibited fecal contamination is a significant reduction in contamination during shipment to market.

EXAMPLE V (treatment of turkeys and chickens)

All of the treatments of turkeys and chickens, as described in Examples I–IV above, should also work when repeated with forms of betaine other than betaine anhydride, such as betaine monohydrate, betaine hydrochloride, and betaine sodium aspartate, or when repeated with a methylamine other than betaine, such as creatine, creatine phosphate, choline, phosphorylcholine, and glycerophosphorylcholine.

EXAMPLE VI (treatment of humans)

A methylamine, including, but not limited to betaine, creatine, creatine phosphate, choline, phosphorylcholine, and glycerophosphorylcholine, in dosage amounts ranging from about 0.05 gram to about 2.0 gram per kilogram of human body weight per day, should also be effective in controlling or stopping diarrhea in humans, wherein the diarrhea is caused by pathogens (i.e., parasites, bacteria, protozoa, and viruses, including toxic agents in food created by spoiling of the food), nutritional factors (i.e., excess mineral salts, excess protein, allergic agents in food, undigestible food components, or poor quality ingredients in food), environmental factors that act as stressors or pollutants (i.e., heat, chilling, or toxins such as from air and/or water pollution), and/or physiological disorders such as those of the digestive tract, pulmonary/circulatory system, liver, kidneys, and/or pancreas, when administered to humans interally, parenterally, buccally, sublingually, orally, or a combination thereof.

The humans thus treated may range in age from newborn infants to geriatric persons of about 100 years in age or even older. Accordingly, when humans having diarrhea are treated with a methylamine, the diarrhea should cease.

EXAMPLE VII (treatment of swine)

A methylamine, including, but not limited to betaine, creatine, creatine phosphate, choline, phosphorylcholine, and glycerophosphorylcholine, in dosage amounts ranging from about 0.05 gram to about 2.0 gram per kilogram of body weight per day, should also be effective in controlling or stopping diarrhea in swine, wherein the diarrhea is caused by pathogens (i.e., parasites, bacteria, protozoa, and viruses, including toxic agents in food created by spoiling of the food), nutritional factors (i.e., excess mineral salts, excess protein, allergic agents in food, undigestible food components, or poor quality ingredients in food), environmental factors that act as stressors or pollutants (i.e., heat, chilling, shipment of the swine such as to a slaughterhouse, or toxins such as from air and/or water pollution), and/or physiological disorders such as those of the digestive tract, pulmonary/ circulatory system, liver, kidneys, and/or pancreas, when administered to swine interally, parenterally, buccally, sublingually, orally, or a combination thereof.

The swine thus treated may range in age from newborn piglings to old sows and boars of about 25 years in age or even older. Accordingly, when swine having diarrhea are treated with a methylamine, the diarrhea should cease.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of treating diarrhea in a warm-blooded vertebrate animal comprising administering to said animal an effective amount of a methylamine.

2. The method of claim 1, wherein administering an effective amount of a methylamine comprises administering a methylamine selected from the group consisting of betaine, creatine, creatine phosphate, choline, phosphorylcholine, glycerophosphorylcholine, and combinations thereof.

3. The method of claim 2, wherein administering an effective amount of betaine comprises administering betaine selected from the group consisting of betaine anhydride, betaine monohydrate, betaine hydrochloride, betaine sodium aspartate, and combinations thereof.

4. The method of claim 1, wherein the diarrhea has a cause selected from the group consisting of pathogens, nutritional factors, environmental factors, physiological disorders, and combinations thereof.

5. The method of claim 4, wherein the environmental factors are selected from the group consisting of heat, chilling, shipment of animals, air pollution toxins, water pollution toxins, and combinations thereof.

6. The method of claim 4, wherein the pathogens are selected from the group consisting of parasites, bacteria, protozoa, and viruses, food toxins, and combinations thereof.

7. The method of claim 1, wherein administering a methylamine to said vertebrate animal comprises administering a methylamine to a vertebrate animal selected from the group consisting of birds and mammals.

8. The method of claim 7, wherein said birds are fowl.

9. The method of claim 8, wherein said fowl are selected from the group consisting of turkeys, chickens, ducks, geese, and guinea fowl.

10. The method of claim 7, wherein said mammals are selected from the group consisting of humans, ruminants, carnivores, horses, and swine.

11. The method of claim 1, wherein administering an effective amount of a methylamine comprises administering a methylamine enterally, parenterally, buccally, sublingually, orally, and a combination thereof.

12. The method of claim 11, wherein orally administering comprises administering a methylamine in a fluid form, tablet form, powder form, and combinations thereof.

13. The method of claim 12, wherein the fluid form comprises a methylamine admixed in a liquid suitable therefor selected from the group consisting of water, a rehydration solution, nutritional fluid, and combinations thereof.

14. The method of claim 11, wherein orally administering comprises administering a methylamine in a human food form, animal feed form, and combinations thereof.

15. The method of claim 1, wherein administering a methylamine comprises administering an effective amount of a methylamine administered to the vertebrate animal in a range from about 0.05 gram to about 2.0 gram of methylamine per kilogram of body weight of the vertebrate animal.

16. The method of claim 1, wherein administering a methylamine comprises administering to the vertebrate animal a methylamine composition including an additional ingredient selected from the group consisting of an excipient, a nutriment, a carrier, a surfactant, a medicament other than a methylamine, and combinations thereof.

17. The method of claim 16, wherein the medicament other than a methylamine is selected from the group consisting of osmolytic polyols, osmolytic amino acids, analgesics, antibiotics, cardiotonics, electrolytes, and combinations thereof.

* * * * *